United States Patent [19]

Yamada et al.

[11] Patent Number: 4,761,409

[45] Date of Patent: Aug. 2, 1988

[54] CEPHEM DERIVATIVES

[75] Inventors: Hirotada Yamada, Nishinomiya, Japan; Naruhito Masai, Gainesville, Fla.; Shinji Ueda, Nishinomiya, Japan; Takao Okuda; Masuhiro Kato, both of Toyonaka, Japan; Masatomo Fukasawa, Nishinomiya, Japan; Masataka Fukumura, Takarazuka, Japan

[73] Assignee: Sumitomo Pharmaceuticals Company, Limited, Osaka, Japan

[21] Appl. No.: 762,560

[22] Filed: Aug. 5, 1985

[30] Foreign Application Priority Data

Aug. 16, 1984 [JP] Japan .................. 59-171098
Oct. 29, 1984 [JP] Japan .................. 59-227299

[51] Int. Cl.$^4$ ............ A61K 31/545; C07D 501/36
[52] U.S. Cl. .......................... 514/206; 540/223; 540/227; 540/226
[58] Field of Search ............ 548/227; 540/227, 223; 514/205, 206

[56] References Cited

U.S. PATENT DOCUMENTS

| | | | |
|---|---|---|---|
| 3,757,012 | 9/1973 | Crast, Jr. ................ | 540/226 |
| 3,928,335 | 12/1975 | Treuner et al. ............ | 424/246 |
| 4,024,133 | 5/1977 | Cook et al. ............... | 544/27 |
| 4,263,291 | 4/1981 | Takaya .................... | 260/243 |
| 4,264,595 | 4/1981 | Numata et al. ............. | 514/206 |
| 4,282,220 | 8/1981 | Borrmann .................. | 544/22 |
| 4,479,947 | 10/1984 | Christensen ............... | 544/28 |
| 4,499,088 | 2/1985 | Takaya et al. ............. | 540/227 X |

FOREIGN PATENT DOCUMENTS

| | | |
|---|---|---|
| 1151151 | 8/1983 | Canada . |
| 0017238 | 10/1980 | European Pat. Off. . |
| 57422 | 8/1982 | European Pat. Off. ........... 542/230 |
| 2285134 | 4/1976 | France . |
| 1575180 | 9/1980 | United Kingdom . |

OTHER PUBLICATIONS

J. Antibiotics, vol. 34, No. 2, pp. 171–185, (1981).

*Primary Examiner*—Donald G. Daus
*Assistant Examiner*—William A. Teoli, Jr.
*Attorney, Agent, or Firm*—Stevens, Davis, Miller & Mosher

[57] ABSTRACT

A cephem derivative represented by the general formula

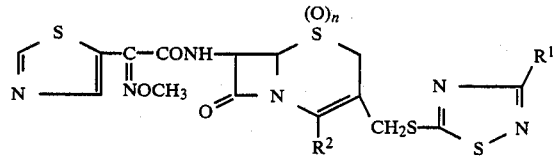

wherein $R^1$ represents hydrogen or methyl, $R^2$ represents carboxyl or esterified carboxyl, and n represents 0 or 1, or a pharmaceutically acceptable salt thereof; intermediates for the cephem derivative or salt thereof; processes for producing these compounds; and a pharmaceutical composition and method for preventing or treating bacterial infectious diseases, wherein the cephem derivative or the salt thereof is used.

23 Claims, No Drawings

CEPHEM DERIVATIVES

The present invention relates to novel cephem derivatives and more particularly to cephem derivatives represented by the general formula

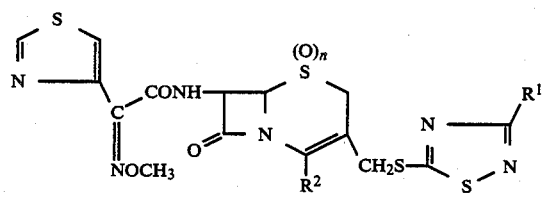

(wherein $R^1$ represents hydrogen or methyl, $R^2$ represents carboxyl or esterified carboxyl, and n represents 0 or 1) and to salts thereof.

The esterified carboxyl group represented by $R^2$ in general formula (I) is, for example, a group represented by the general formula

—COOR (wherein R represents an alkanoyloxyalkyl, alkoxycarbonyloxyalkyl, or (5-alkyl-2-oxo-1,3-dioxolen-4-yl)methyl group). Accordingly, the esterified cephem derivatives in the present invention include, e.g. alkanoyloxyalkyl esters, alkoxycarbonyloxyalkyl esters, and (5-alkyl-2-oxo-1,3-dioxolen-4-yl)methyl esters of the carboxylic acids of general formula (I). In these esters; alkanoyl groups include those of 2-6 carbon atoms, e.g. acetyl, propionyl, butyryl, isobutyryl, valeryl, pivaloyl, and hexanoyl; alkoxy groups include those of 1-6 carbon atoms, e.g. methoxy, ethoxy, propoxy, isopropoxy, and n-butoxy; and alkyl groups include those of 1-4 carbon atoms, e.g. methyl, ethyl, propyl, isopropyl, butyl, isobutyl, and sec-butyl.

Individual examples of the above esters are as follows: Examples of the alkanoyloxyalkyl esters are acetoxymethyl, propionyloxymethyl, butyryloxymethyl, isobutyryloxymethyl, valeryloxymethyl, pivaloyloxymetyl, hexanoyloxymethyl, 1-acetoxyethyl, 1-propionyloxyethyl, 1-pivaloyloxyethyl, and 1-acetoxypropyl esters. Examples of the alkoxycarbonyloxyalkyl esters are methoxycarbonyloxymethyl, 1-methoxycarbonyloxyethyl, 1-methoxycarbonyloxypropyl, ethoxycarbonyloxymethyl, propoxycarbonyloxymethyl, 1-ethoxycarbonyloxyethyl, and 1-propoxycarbonyloxyethyl esters. Examples of the (5-alkyl-2-oxo-1,3-dioxolen-4-yl)methyl esters are (5-methyl-2-oxo-1,3-dioxolen-4-yl)methyl and (5-ethyl-2-oxo-1,3-dioxolen-4-yl)methyl esters.

Compounds of general formula (I) wherein $R^2$ is carboxyl may form their salts (these are included in the scope of the present invention). Such salts are preferably; alkali metal salts, e.g. sodium salts and potassium salts; alkaline earth metal salts, e.g. calcium salts and magnesium salts; organic amine salts, e.g. triethylamine salts, diethanolamine salts, pyridine salts, picoline salts, N,N-dibenzylethylenediamine salts, morpholine salts, and procaine salts; and amino acid salts, e.g. L-arginine salts and L-lysine salts.

In the 7-positional side chain

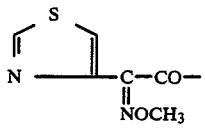

in general formula (I), there is a geometrical isomerism of syn and anti. Of these isomers, preferred are compounds having a syn configuration represented by

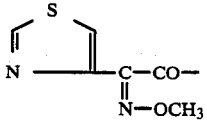

in the 7-positional side chain.

In recent years antibiotics of the cephem group are under remarkable development as therapeutic agents for the treatment of infections diseases. Compounds of this group are now commercially available which have high antimicrobial activity and wide antimicrobial spectra. However, these compounds are scarcely absorbed when orally administered, so that therapeutic effect is achievable only when administered parenterally.

Compounds such as cephalexin, cefatrizine, and cefaclor, although in use as cephem antibiotics for oral administration, are slightly inferior in antimicrobial activity and width of the antimicrobial spectrum and are ineffective on resistant bacteria which produce β-lactamase. It is therefore desired to develop a compound improved in the above noted properties.

On the other hand, there are in clinical use certain penicillin compounds which, so-called prodrugs, have been improved in oral absorbability by esterification of the carboxyl group of penicillin. It is generally considered that the esterified compound absorbed in the living body is hydrolyzed into the original carboxylic acid, viz. the parent compounds, by enzymes present, for example, in the serum or tissues of the body, thus exhibiting the effect. Similar modificiations of cephalosporin compounds have been attempted, but no compound having an oral absorbability sufficient for clinical use has been found until now. That is, some ester groups effective in penicillin compounds for enhancing the oral absorbability are not always so effective in cephalosporin compounds.

The present inventors made extensive studies of cephalosporin compounds for improvement in oral absorbability by the prodrug method. It has proved from these studies that the absorbability after oral administration is unpredictable at all and much depends upon the structure and properties of the parent compound chosen.

Based on such knowledge, the present invention has been accomplished. Among the compounds of the invention represented by general formula (I), those of the formula wherein n is O and $R^2$ is esterified carboxyl have such superior properties as good oral absorbability unexpectable from known compounds of analogous structure and high rates of esterase-catalyzed hydrolysis. Moreover the parent compounds, $R^2$'s of which are carboxyl groups, (these ester compounds, when absorbed after oral administration, are converted into the parent compounds and then can exhibit antimicrobial effect) are highly excretable into urine. This is also one of the features of the present compounds. Hence these ester compounds are very valuable as oral drugs in the prevention or treatment of bacterial infectious diseases.

Among the compounds of the invention, represented by general formula (I), those of the formula wherein n is O and $R^2$ is carboxyl have high antimicrobial activity on gram-postive bacteria and gram-negative bacteria including on β-lactamase-producing bacteria. These compounds, hence useful as such, are also useful as intermediates for the parent compounds having esterified carboxyl as $R^2$.

Furthermore, among the compounds of the invention, sulfoxide compounds, i.e. the compounds of general formula (I) wherein n is 1 are useful as intermediates in the production of the parent compounds having esterified carboxyl as $R_2$. Further details of these intermediates will be described later.

In the next place, description is given on processes for producing the cephem compounds of the present invention.

The compounds of the invention can be produced by processes which themselves are known, for example, as follows:

Process (a)

A derivative of 7-amino-3-(1,2,4-thiadiazol-5-yl)thiomethyl-3-cephem-4-carboxylic acid represented by the general formula

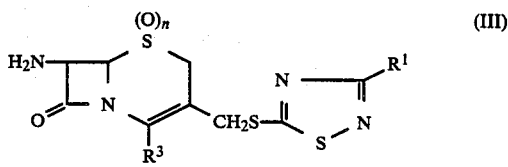

(wherein n and $R^1$ are as defined above and $R^3$ has the same meaning as does the above $R^2$ or represents protected carboxyl) is acylated with a compound represented by the formula

and if necessary, the protecting group is removed or the carboxyl group is esterified.

Process (b)

A compound represented by the general formula

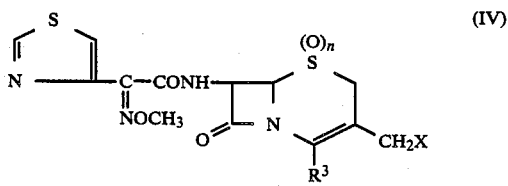

(wherein $R^3$ and n are as defined above and X represents —OCOCH$_3$ or halogen) is subjected to nucleophilic substitution by a 3-(substituted or unsubstituted)-1,2,4-thiadiazole-5-thiol group for the 3-positional X, and if necessary, the protecting group is removed or the carboxyl group is esterified.

Process (c)

The acyl group attached to the 7-positional nitrogen atom of the compound of general formula (I) is derived from another acyl group.

Processes (a), (b), and (c) are described below in more detail.

Process (a)

A compound represented by the general formula

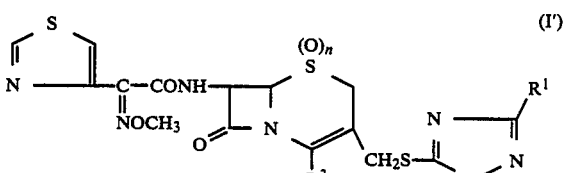

wherein n, $R^1$, and $R^3$ are as defined above) or a salt thereof can be obtained by reacting the carboxylic acid represented by formula (II) above or a reactive derivative thereof with a compound of general formula (III) above or a salt or derivative thereof. When the group represented by $R^3$ is carboxyl or a salt thereof, a compound of the invention represented by general formula (I) can be obtained, if necessary, further by esterification of the above product. Moreover when the group represented by $R^3$ is protected carboxyl, the protecting group is removed from the above product, and if necessary, the resulting compound is esterified.

The above reactive derivative of a carboxylic acid represented by formula (II) means a corresponding compound having a reactive carboxyl derivative residue which can react with a compound represented by general formula (III) above to form an amido linkage. Examples of the reactive derivative are acid halides, acid anhydrides, acid azolides, active esters, and acid azides of the compound represented by formula (II). More particularly, examples thereof are; mixed acid anhydrides with dialkyl phosphates, phenyl phosphoric acid, diphenyl phosphate, dibenzyl phosphate, dialkylphosphorous acids, methanesulfonic acid, toluenesulfonic acid, naphthalenesulfonic acid, alkyl hydrogencarbonates, aliphatic carboxylic acids, (e.g. pivalic acid, pentanoic acid, isopentanoic acid, and 2-ethylbutanoic acid), and aromatic carboxylic acids; symmetric acid anhydride; acid azolides with imidazole, substituted imidazole, dimethylpyrazole, triazole, and tetrazole; and active esters, e.g. cyanomethyl ester, methoxymethyl ester, p-nitrophenyl ester, 2,4-dinitrophenyl ester, trichlorophenyl ester, pentachlorophenyl ester, methanesulfonylphenyl ester, phenylthiophenyl ester, p-nitrophenyl thioester, p-cresyl thioester, carboxymethyl thioester, pyranyl ester, pyridyl ester, piperidyl ester, 8-quinolyl thioester, and esters with N,N'-dimethylhydroxylamine, 1-hydroxy-2(1H)-pyridone, N-hydroxysuccinimide, N-hydroxyphthalimide, and hydroxybenzotriazol.

When the compound represented by formula (II) is used in the form of free acid or a salt thereof, the amidation can be carried out in the presence of a condensing agent. The condensing agent includes, for example, N,N'-dicylohexylcarbodiimide, N-cyclohexy-1N'-morpholinoethylcarbodiimide, N-cyclohexyl-N'-(4-diethylaminocyclohexyl)carbodiimide, N,N'-diethyl-carbodiimide, N,N'-diisopropylcarbodiimide, N-ethy-1N'-(3-dimethylaminopropyl)carbodiimide, N,N'-carbonylbis-(2-methylimidazole), pentamethyleneketene-N-cyclohexylimine, diphenylketene-N-cyclohexylimine, diphenylketene-N-cyclohexylimine, alkoxyacetylenes, 1-alkoxy-1-chloroethylenes, trialkyl phosphites, ethyl polyphosphate, isopropyl polyphosphate, phosphorus oxychloride, phosphorus trichloride, thionyl chloride, oxalyl chloride, triphenylphosphine, 2-ethyl-7-hydroxybenzisoxazolium salt, 2-ethyl-5-(m-sufonyl)isoxazolium hydroxide inner salt, (chloromethylene)dimethylammonium chloride, and Vilsmeier's reagent which is prepared by reacting phosphorus oxychloride with dimethylformamide.

Suitable salts of the compound of general formula (III) above include, for example; salts of the compound with alkali or alkaline earth metals such as sodium, potassium, and calcium; salts thereof with organic bases such as trimethylamine, triethylamine, quinoline, and such as collidine; salts thereof with organic sulfonic acids such as toluenesulfonic acid, naphthalenesuffonic acid, and tetralinsulfonic acid; and salts thereof with inorganic acids such as hydrochloric acid, sulfuric acid, and nitric acid.

The protected carboxyl group represented by $R^3$ in general formula (III) above is a carboxyl group protected by, for example, esterification or amidation. Preferred protecting groups of the carboxyl group are those which, after acylation, are readily removed to give free carboxylic acid residues by suitable reaction, for example, hydrolysis or alcoholysis in an acidic or weak alkaline medium, hydrogenolysis, reductin, oxidation, nucleophilic substitution, photochemical reaction, or enzymatic reaction. Such protected carboxylic derivates include known protected carboxylic esters, e.g. silyl ester, organic tin ester, tolenesulfonylethyl ester, p-nitrobenzyl ester, diphenylmethyl ester, trityl ester, trichloroethyl ester, phthalimidomethyl ester, 2-nitrobenzyl ester, 2,2'-dinitrobenzyl ester, and t-butyl ester.

When the derivative having a protected carboxyl group is a silyl ester, the other site that can be silylated, i.e. the amino group, of the derivative may be silylated as well. Such compounds can be cited as examples of the derivative of the compound represented by general formula (III).

The reaction of the compound represented by formula (II) or a reactive derivative thereof with the compound represented by general formula (III) or a salt or derivative thereof can be carried out by applying amidation techniques which are used in peptide chemistry, penicillin and cephalosporin chemistry, and other related fields. More specifically, this reaction is effected in an inert solvent consisting of a polar solvent, a nonpolar solvent, or a mixture of them: a polar solvent such as dichloromethane, chloroform, acetone, tetrahydrofuran, dioxane, acetonitrile, methyl isobutyl ketone, dimethylformamide, dimethylacetamide, dimethylsulfoxide, hexamethylphosphoric triamide, or sulfolane; and/or nonpolar solvent such as benzene, toluene, petroleum ether, or n-hexane. In certain cases, mixtures of water and these solvents can be used. The above reaction can be carried out at any possible temperature, but usually up to 50° C.

In the above described manner, the compound represented by general formula (I') above can be prepared. When the group represented by $R^3$ is carboxyl or a salt thereof, the compound of the present invention represented by general formula (I) wherein $R^2$ is esterified carboxyl can be prepared by reacting the obtained compound of general formula (I') with an esterifying agent.

This esterification can be accomplished by the methods which themselves are known. For instance, a desired ester can be prepared by reacting a compound of general formula (I') wherein $R^3$ is an alkali metal salt of carboxyl with a halide (preferably, iodide, bromide, or chloride) of the alcohol residue of the intended ester in an inert solvent. A known method of esterification in the presence of a crown ether or a phase transfer catalyst can be applied to this reaction. The esterification is favorably carried out in the presence of a base, e.g. an organic base such as triethylamine or an inorganic base such as sodium carbonate or potassium carbonate.

When an alcohol is used as an esterifying agent, the reaction is preferably carried out in the presence of a condensing agent. Such condensing agents include; carbodiimide compounds, e.g. N,N'-dicyclohexylcarbodiimide, N,N'-diethylcarbodiimide, and N-cyclohexyl-N'-(4-diethylaminocyclohexyl)carbodiimide; sulfonic acid esters of N-hydroxybenzotriazole derivatives, e.g. 1-(4-chlorobenzensulfonyloxy)-6-chloro-1H-benzotriazole; benzenesulfonyl chloride; and so-called Vilsmeier's reagent, which is prepared by reacting dimethylformamide with a halogen compound such as thioxyl chloride or phosphorus oxychloride.

The reaction temperature is not particularly limited, but it is usually up to 50° C. Inert solvents suitable for the above amidation can also be used in this esterification.

The product of the esterification, when a sulfide of general formula (I) wherein n is 0 is used as a starting material, may contain 2-cephem isomer thereof as an impurity. The 2-cephem isomer can be removed by recrystallization, reprecipitation, column chromatography, etc. Alternatively, the 2-cephem-containing product is converted into 3-cephem-1-oxide form by oxidation with m-chloroperbenzoic acid, peracetic acid, periodic acid, or the like, and then the oxide is reduced, for example, by phosphorus trichloride or by a combination of stannous chloride with acetyl chloride, whereby the intended 3-cephem ester product can be obtained in substantially pure form. The sulfur atom of the cephem ring can be oxidized according to the usual method. This reaction may yield the (S)-configuration and/or (R)-configuration oxide depending upon the oxidant used. Both the oxides are included in the scope of the present invention. The oxidation and reduction of the sulfur atom of the cephem ring are described, for example, in "Cephalosporins and Penicillins, Chemistry and Biology" edited by E. Flynn (Academic press, 1972), Chapter 4, p. 135.

The starting compound represented by formula (II) is prepared, for example, according to a process described in U.S. Pat. No. 4,282,220 or 4,263,291.

The starting compound represented by general formula (III) can be prepared according to known processes [described in e.g. U.S. Pat. Nos. 3,979,383, 4,312,986, and 4,446,318, DT Patent No. 2,804,896, and Japanese patent application Laid-Open No. 49,383/70 (Central Patent Index 80-37277 C/21, Derwent Publications, LTD.), for example, a process comprising reacting 7-aminocephalosporanoic acid with 3-(substituted or unsubstituted)-1,2,4-thiadiazole-5-thiol.

The compound in ester form represented by general formula (III) can be prepared according to processes which themselves are known.

For instance, a compound represented by the general formula

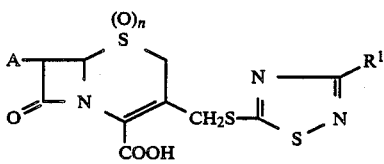

(wherein $R^1$ and n are as defined above and A represents amino or protected amino) or a salt thereof is reacted with a compound represented by the general formula

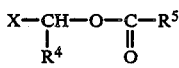

(wherein X represents halogen, $R^4$ represents hydrogen or alkyl, and $R^5$ represents alkyl or alkoxy) or a compound represented by the general formula

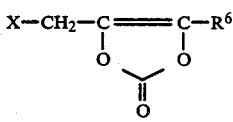

(wherein X represents halogen and $R^6$ represents alky), whereby an ester compound represented by the general formula

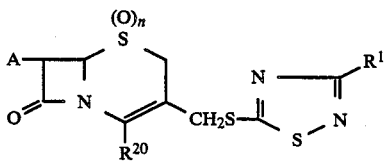

[wherein $R^1$, n, and A are as defined above and $R^{20}$ represents

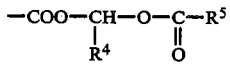

($R^4$ and $R^5$ are as defined above) or

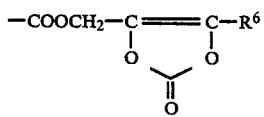

($R^6$ is as defined above)] can be obtained. When A is protected amino, a compound represented by the general formula

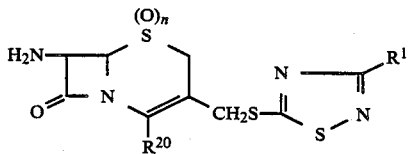

(wherein $R^1$, $R^{20}$, and n are as defined above) can be obtained by removing the protecting group. Examples of the protected amino group of the compound represented by general formula (IIIa) are formylamino, 1-methyl-2-methoxycarbonylvinylamino, substituted or unsubstituted benzylideneamino, t-butoxycarbonylamino, benzyloxycarbonylamino, p-nitrobenzyloxycarbonylamino, p-methoxybenzyloxycarbonylamino, tritylamino, phthalimido, phenylacetylamino, and thienylacetylamino groups. Removal of the protecting group from each of these protected groups is carried out by a suitable method such as acid hydrolysis, decomposition by reduction, decomposition by hydrazine, hydrolysis by conversion to imino chloride-imino ether using phosphorus pentachloride, etc. owing to each protected group.

Such known methods are described in G.B. Patent No. 1,406,113, Journal of Medicinal Chemistry, 9, 444 (1966), The Journal of Antibiotics, 24, 767 (1971), Synthesis 1983, 549, and Japanese Patent Application Laid-Open Nos. 159,496/83, 4190/85, and 51,193/85.

Process (b)

The compound of the present invention represented by general formula (I) can be obtained by nucleophilic substitution by 3-(substituted or unsubstituted)-1,2,4-thiadiazole-5-thiol for the 3-positional X of the compound represented by the general formula

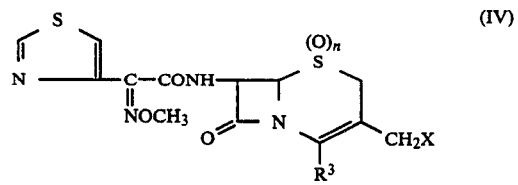

(wherein $R^3$, n, and X are as defined above). Method themselves known are applicable to this nucleophilic substitution [described in, e.g. "Cephalosporins and Penicillins, Chemistry and Biology" edited by E. Flynn (Academic Press, 1972), Chapter 4, p. 158, Ger. Patent No. 2,809,058, "Recent Advances in the Chemistry of β-Lactam Antibiotics", Cambridge, England, 28–30, June, 1976, The Chemical Society, Burlington House, London W1V OBN, p. 109, and Tetrahedron Letters, 22, 3915 (1981)].

The compound of general formula (IV) can be prepared by reacting, similarly to the reaction for preparing the compound of general formula (I'), the carboxylic acid of formula (II) with the compound represented by the general formula

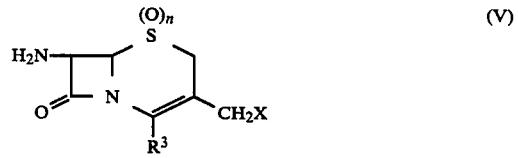

(wherein X, $R_3$, and n are as defined above). The compound represented by general formula (IV) wherein X is halogen can also be prepared, for instance, by the method described in "Recent Advances in the Chemistry of β-Lactam Antibiotics, Cambridge, England, 28–30 June, 1976" edited by J. Elks, published by The Chemical Society, Burlington House, London W1V OBN, p. 106; and Tetrahedron Letters, 22, p. 3915

(1981). The above halogen includes iodine, bromine, and chlorine atoms.

Process (c)

For example, there are the following processes (1), (2), and (3) for deriving chemically the 7-positional acyl group of the compound represented by general formula (I) from another acyl group.

(1) A process comprising reacting a carboxylic acid represented by the formula

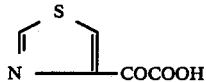
(VI)

or a reactive derivative thereof with a compound represented by general formula (III) or a salt or derivative thereof, and reacting the resulting compound represented by the general formula

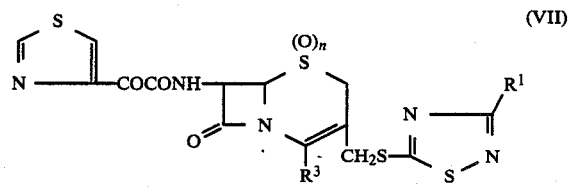
(VII)

(wherein $R^1$, $R^3$, and n are as defined above) with methoxyamine, followed if necessary, by removal of the protecting group and esterification of the carboxyl group to give a compound of the present invention represented by general formula (I).

(2) A process comprising nucleophilic substitution by 3-(substituted or unsubstituted)-1,2,4-thiadiazole-5-thiol for the 3-positional X of a compound represented by the general formula

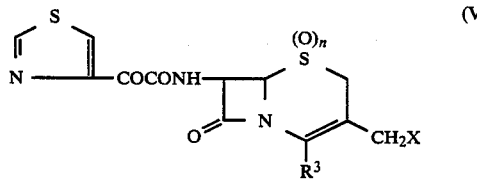
(VIII)

(wherein $R^3$, X, and n are as defined above), and reacting the resulting compound represented by the general formula

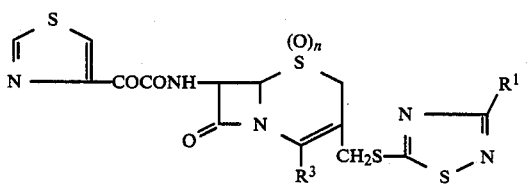
(IX)

(wherein $R^1$, $R^3$, and n are as defined above) or a salt thereof with methoxyamine, followed if necessary, by removal of the protecting group and esterification of the carboxyl group to give a compound of the present invention represented by general formula (I).

(3) A process comprising reacting a compound represented by the general formula

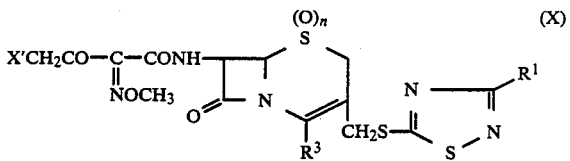
(X)

(wherein $R^1$, $R^3$, and n are as defined above and X' represents chlorine or bromine) or a salt thereof with thioformamide, followed if necessary, by removal of the protecting group and esterification of the carboxyl group to give a compound of the present invention represented by general formula (I).

The carboxylic acid represented by formula (VI) is a known compound, which is described, for example, in U.S. Pat. No., 4,282,220.

The reaction of the compound represented by formula (VI) with the compound represented by general formula (III) to yield the compound represented by general formula (VII) can be carried out in the same manner as the reaction of the compound represented by formula (II) with the compound represented by general formula (III) to yield the compound represented by general formula (I).

The reaction of the compound represented by general formula (VII) with methoxyamine can be carried out according to known methods (e.g. the methods of GB Patent Nos. 1,600,735 and 1,600,736).

The nucleophilic substitution for the 3-positional X of the compound represented by general formula (VIII) can be carried out in the same manner as described in (b) above.

The compound represented by general formula (X) can also prepared according to known methods (e.g. the method described in GB Patent No. 1,602,876).

The reaction of the compound represented by general formula (X) with thioformamide to yield the compound represented by general formula (I) can also be carried out under known conditions.

As stated before, the compound of the present invention represented by general formula (I) wherein $R^2$ is esterified carboxyl and n is 0 is useful as an antibiotic drug suitable for oral administration because of its excellent oral absorbability. For oral administration, the compound of the invention can be made up into capsules, powders, granules, tablets, and the like according to conventional formulations for oral dosage. These pharmaceutical compositions may contain usual excipients, binders, lubricants, disintegrating agents, etc. The compound of general formula (I) wherein n is 0 can be made up also into rectal dosage form (e.g. suppository or retention clyster) or injectable form.

Suitable doses of the compound, though dependent upon the age, weight, and condition of patients, are generally 0.1 to 2 g per day for an adult, such a quantity of the compound may be administered in single or divided doses.

To manifest excellent properties of compounds of the invention, results of tests thereof for oral absorbability and for in vitro antimicrobial activity are shown below.

| Results of oral absorbability tests | |
|---|---|
| Test compd. (Example No.) | Urinary excretion rate in mice after oral administration (dose: 50 mg/kg) |
| 6 | 32% |
| 15 | 32% |

| Results of antimicrobial activity tests | | | | | |
|---|---|---|---|---|---|
| | MIC (μg/ml) | | | | |
| Test compd. (Example No.) | Staphylococcus aureus 209P | Staphylococcus epidermidis IAM1296 | Escherichia coli NIHJ JC-2 | Serratia marcescens X100 | Citrobacter freundii GN346 |
| 1 | 0.10 | 1.56 | 0.10 | 0.78 | 0.78 |
| 2 | 0.20 | 1.56 | 0.20 | 0.78 | 0.78 |

The present invention is illustrated in more detail by the following examples; however, the invention is not limited by these example.

EXAMPLE 1

7-[(Z)-2-Methoxyimino-2-(thiazol-4-yl)acetamido]-3-(3-methyl-1 2,4-thiadiazol-5-yl)thiomethyl-3-cephem-4-carboxylic acid (a) A solution of 1-hydroxybenzotriazole (13.5 g) in dimethylformamide (100 ml) was added to a solution of (z)-2-methoxyimino-2-(thiazol-4-yl) acetic acid (18.6 g) in dimethylformamide (100 ml). Further dicyclohexylcarbodiimide (22.7 g) was added and this reaction mixture was stirred at 30° C. for 2 hr. The precipitated urea compound was removed by filtration, and the filtrate was added dropwise to cold water (1250 ml). The mixture was stirred for 1 hr under cooling with ice and the formed precipitate was collected, washed with water, and dried in vacuo to give an active ester compound (29.3 g).

IR (nujol): 1820, 1725 cm$^{-1}$.

$^1$H-NMR (DMSO-d$_6$)δppm: 4.00 (s, 3H), 7.6–8.4 (m, 4H), 8.38 (d, 1H), 9.17 (d, 1H).

(b) 7-Amino-3-(3-methyl-1,2,4-thiadiazol-5-yl)-thiomethyl-3-cephem-4-carboxylic acid (1.72 g) was added to a solution of triethylamine (1.01 g) in dimethyl formamide (8 ml), and while cooling with ice, the above active ester (1.82 g) was added. The mixture was stirred for 4 hr. This reaction mixture was poured into water (100 ml), and the mixture was adjusted to pH 2.0 with 2N-HCl under cooling with ice. The formed crystals were filtered off, washed with water, and dried over P$_2$O$_5$ in vacuo to give the title compound (1.65 g) in crude form. This compound was subjected to reverse-phase liquid chromatography [column: Lichroprep ®RP-8, size B (310×25 mm), supplied by Merck Co.; mobile phase: 0.01 M phosphate buffer-acetonitrile (88:22 v/v)], and the necessary fractions were combined, concentrated in vacuo, and subjected to acidification to give the title compound in purified form.

$^1$H NMR (DMSO-d$_6$)δppm: 2.52 (s, 3H, CH$_3$), 3.55, 3.76 (ABq, 2H, J=18 Hz, C$_2$-H$_2$), 3.91 (s, 3H, OCH$_3$), 4.24, 4.63 (ABq, 2H, J=13 Hz, C$_3$-CH$_2$), 5.16 (d, 1H, J=5 Hz, C$_6$-H), 5.83 (dd, 1H, J=8.5 Hz, C$_7$-H), 7.93 (d, 1H, J=2 Hz, 5-positional H on thiazole ring), 9.15 (d, 1H, J=2 Hz, 2-positional H on thiazole ring), 9.68 (d, 1H, J=8 Hz, —CONH—).

EXAMPLE 2

7-[(Z)-2-Methoxyimino-2-(thiazol-4-yl)acetamido]-3-(1,2,4-thiadiazol-5-yl)thiomethyl-3-cephem-4-carboxylic acid 7-Amino-3-(1,2,4-thiadiazol-5-yl)thiomethyl-3-cephem-4-carboxylic acid (3.31 g) and the active ester (3.63 g) from (a) of Example 1 were added successively to a solution of triethylamine (2.02 g) in dimethylformamide (15 ml) and the mixture was stirred for 5 hr under cooling with ice. Then the reaction mixture was poured into diethyl ether (300 ml) with stirring. After standing, the upper diethyl ether layer was removed and the lower oily layer was dried in vacuo, giving a caramel-like substance containing the title compound. This substance was dissolved in aq. NaHCO$_3$, and subjected to reverse phase liquid chromatography [column: Lichroprep ®RP-8, 2 columns of C size in series (supplied by Merck Co.); mobile phase: 0.01 M phosphate buffer-acetonitrile (86:14, v/v)]. The necessary fractions were combined, concentrated in vacuo, subjected to acidification with 6N-HCl. The precipitates were collected and dried over P$_2$O$_5$ in vacuo to give the title compound (0.79 g) in purified form. Additionally the title compound (0.28 g) was obtained by extraction of the filtrate with ethyl acetate, drying the ethyl acetate layer over MgSO$_4$, and evaporation to dryness.

$^1$H NMR (DMSO-d$_6$)δppm: 3.58, 3.77 (AB$_q$, 2H, J=18 Hz, C$_2$-H$_2$), 3.91 (s, 3H, CH$_3$), 4.32, 4.60 (AB$_q$, 2H, J=13Hz, C$_3$-CH$_2$), 5.17 (d, 1H, J=5 Hz, C$_6$-H), 5.84 (dd, 1H, J=8 and 5 Hz, C$_7$-H), 7.94 (d, 1H, J=2 Hz, 5-positional H on thiazole ring), 8.72 (s, 1H, 3-positional H on thiadiazole ring), 9.15 (d, 1H, J=2 Hz, 2-positional H on thiazole ring), 9.68 (d, 1H, J=8 Hz, —CONH—).

A sodium salt of the title compound was obtained by dissolving the above product (0.79 g) in a solution of NaHCO$_3$ (0.135 g) in water (10 ml), followed by lyophilization.

EXAMPLE 3

Pivaloyloxymethyl 7-[(Z)-2-methoxyimino-2-(thiazol-4-yl)acetamido]-3-(3-methyl-1,2,4-thiadiazol-5-yl)thiomethyl-3-cephem-4-carboxylate Pivaloyloxymethyl iodide (242 mg) was added to a solution of sodium 7-[(Z)-2-methoxyimino-2-(thiazol-4-yl)acetamido]-3-(3-methyl-1,2,4-thiadiazol-5-yl)-thiomethyl-3-cephem-4-carboxylate (534 mg) in dimethylformamide (5 ml) under cooling with ice. The mixture was stirred for 30 min and then poured into a mixture of ethyl acetate (30 ml) and water (20 ml, adjusted to pH 3 with dil. HCl) with stirring. The ethyl acetate layer was separated, washed successively with water (20 ml, adjusted to pH 3 with dil. HCl), 10% aqueous K$_2$HPO$_4$ solution (20 ml) twice, and saturated saline water (20 ml), dried over MgSO$_4$, and concentrated in vacuo. The residue was dissolved in diethyl ether (20 ml) and the solution was added dropwise to petroleum ether (100 ml) with stirring. The formed crystals were filtered, and dried in vacuo to give the title compound (500 mg).

$^1$H NMR (DMSO-d$_6$)δ ppm: 1.14 [s, 9H, (CH$_3$)$_3$], 2.50–2.52 (3-positional CH$_3$ on thiazole ring, overlapping with peaks due to DMSO used for measurement), 3.60, 3.82 (ABq, 2H, J=18 Hz, C$_2$—H$_2$), 3.90 (s, 3H, —OCH$_3$), 4.23, 4.58 (ABq, 2H, J=13 Hz, C$_3$—CH$_2$), 5.20 (d, 1H, J=5 Hz, C$_6$—H), 5.8–6.0 (m, 3H, C$_7$—H —COOCH$_2$O), 7.95 (d, 1H, J=2 Hz, 5-positional H on thiazole ring), 9.16 (d, 1H, J=2 Hz, 2-positional H on thiazole ring), 9.70 (d, 1H, J=8 Hz, —CONH—).

EXAMPLE 4

1-Ethoxycarbonyloxyethyl 7-[(Z)-2-methoxyimino-2-(thiazol-4-yl)acetamido]-3-(3-methyl-1,2,4-thiadiazol-5-yl)thiomethyl-3-cephem-4-carboxylate 1-Bromoethylethyl carbonate (472 mg) was added to a solution of sodium 7-[(Z)-2-methoxyimino-2-(thiazol-4-yl)acetamido]-3-(3-methyl-1,2,4-thiadiazol-5-yl)thiomethyl-3-cephem-4-carboxylate (536 mg) in dimethylformamide (5 ml) under cooling with ice. The mixture was stirred for 3 hr and then poured into a mixture of ethyl acetate (120 ml) and water (20 ml, adjusted to pH3 with dil. HCl) with stirring. The ethyl acetate layer was separated, washed successively with water (20 ml, adjusted to pH 3 with dil. HCl), 10% aqueous K$_2$HPO$_4$ solution (20 ml) twice, and saturated saline water (20 ml), drived over MgSO$_4$, concentrated in vacuo, and the residue was added dropwise to petroleum ether. The formed crystals were filtered and dried in vacuo to give the title compound (325 mg). This product was found to contain the Δ$^2$ isomer.

EXAMPLE 5

1-Ethoxycarbonyloxyethyl 7-(Z)-2-methoxyiino-2-(thiazol-4-yl)acetamido]-3-(3-methyl-1,2,4-thiadiazol-5-yl)thiomethyl-3-cephem-4-carboxylate-1-oxide A solution of m-chloroperbenzoic acid (52.4 mg) in chloroform (1 ml) was added dropwise to a solution of the Δ$^2$ isomer-containing compound (200 mg) from Example 4 in chloroform (1 ml), and the mixture was stirred at room temperature for 1.5 hr. The formed crystals were filtered, washed with chlorofrom, and dried in vacuo to give the title compound (150 mg).

$^1$H NMR (DMSO-d$_6$)δ(ppm):

1.18, 1.23 (t×2, 3H, —CH$_2$CH$_3$), 1.56 (d, 3H, J=5Hz, —CH—), 
|
CH$_3$ 2.53 (s, 3H, 3-positional CH$_3$ on thiadiazole ring),
3.82 (d, 1H, J=18Hz, C$_2$—H), 3.93 (s, 3H, —OCH$_3$), 3.98–4.25 (m, 4H, C$_2$—H, —CH$_2$CH$_3$, C$_3$—CH), 4.63–4.73 (apparent t, 1H, C$_3$—CH), 5.00 (m, 1H, C$_6$—H), 5.98 (m, 1H, C$_7$—H), 6.92 (m, 1H, —CH—),
|
CH$_3$ 7.98 (s, 1H, 5-positional H on thiazole ring),
9.15 (m, 2H, 2-positional H on thiazole ring, —CONH—)

EXAMPLE 6

1-Ethoxycarbonyloxyethyl 7-[(Z)-2-methoxyimino-2-(thiazol-4-yl)acetamido]-3-(3-methyl-1,2,4-thiadiazol-5-yl)thiomethyl-3-cephem-4-carboxylate Stannous chloride dihydrate (84.6 mg) was added to a solution of 1-ethoxycarbonyloxyethyl 7-[(Z)-2-methoxyimino-2-(thiazol-4-yl)acetamido]-3-(3-methyl-1,2,4-thiadiazol-5-yl)thiomethyl-3-cephem-4-carboxylate-1-oxide (96.6 mg) in dimethylformamide (2 ml), and then acetyl chloride (0.38 ml) was added dropwise to the mixture with stirring while cooling with ice. After further stirring in 20° C. for 15 min, the reaction mixture was poured into a mixture of water (20 ml) and ethyl acetate (15 ml). The ethyl acetate layer was separated and the aqueous layer was extracted twice with ethyl acetate (15 ml). The whole ethyl acetate layer combined was dried over MgSO$_4$, concentrated in vacuo, and the residue was added to petroleum ether (30 ml). The resulting crystals were filtered, washed with petroleum ether, and dried in vacuo to give the title compound (30 mg).

$^1$H NMR (DMSO-d$_6$)δ(ppm):

1.17, 1.22 (t×2, 3H, J=7Hz, —CH$_2$CH$_3$), 1.52 (d, 3H, J=5Hz, —CH—),
|
CH$_3$ 2.53 (s, 3H, 3-positional CH$_3$ on thiadiazole ring), 3.62, 3.82 (ABq, 2H, J=18Hz, C$_2$—H$_2$), 3.91 (s, 3H,OCH$_3$), 4.02–4.30 (m, 3H, —CH$_2$CH$_3$, C$_3$—CH), 4.45–4.55 (apparent t, 1H, C$_3$—CH), 5.21
(apparent t, 1H, C$_6$—H), 5.90 (dd, 1H, C$_7$—H), 6.87 (m, 1H, —CH—),
|
CH$_3$ 7.94 (d, 1H, 5-positional H on thiazole ring),
9.15 (d, 1H, 2-positional H on thiazole ring),
9.68 (d×2, 1H, —CONH—)

EXAMPLE 7

1-Pivaloyloxyethyl 7-[(Z)-2-methoxyimino-2-(thiazol-4-yl)acetamido]-3-(3-methyl-1,2,4-thiadiazol-5-yl)thiomethyl-3-cephem-4-carboxylate Sodium iodide (6.0 g) in acetonitrile (33 ml) was heated to 40° C. After addition of 1-chloroethyl pivalate (1.65 g), the mixture was stirred for 30 min at that temperature, and insoluble matter was removed by filtration. Petroleum ether (200 ml) and a 5% aqueous sodium thiosulfate solution (20 ml) were added to the filtrate, and the mixture was shaken. The petroleum ether layer was separated, washed several times with a 5% aqueous sodium thiosulfate solution, dried over MgSO$_4$, concentrated in vacuo, and the residue was added to a solution cooled to 5° C. of sodium 7-[(Z)-2-methoxyimino-2-(thiazol-4-yl)acetamido]-3-(3-methyl-1,2,4-thiadiazol-5-yl)thiomethyl-3-cephem-4-carboxylate (536 mg) in dimethylformamide (5 ml). The mixture was stirred at −5° C. for 45 min and then poured into a mixture of water (20 ml) and ethyl acetate (20 ml). The ethyl acetate layer was separated and the aqueous layer was extracted twice with ethyl acetate (20 ml). The whole ethyl acetate layer combined was dried over MgSO₄, concentrated in vacuo, and the residue was added to petroleum ether (30 ml). The formed crystals were filtered, washed with petroleum ether, and dried in vacuo to give the title compound (340 mg).

¹H NMR (DMSO-d₆)δ(ppm):

1.11, 1.13 [s×2, 9H, —(CH₃)₃], 1.49 (d, 3H, —CH—)
                                          |
                                          CH₃

2.52 (s, 3H, 3-positional CH₃ on thiadiazole ring),
3.60 (dd, 1H, J=18, 4Hz, C₂—H),
3.80 (d, 1H, J=18Hz, C₂—H), 3.91 (s, 3H, OCH₃),
4.25 (dd, 1H, J=13, 4Hz, C₃—CH), 4.49 (apparent t, 1H, J=14Hz, C₃—CH), 5.21
(m, 1H, C₆—H), 5.89 (m, 1H, C₇—H), 6.91, 6.98 (q×2, 1H, —CH—),
                                                         |
                                                         CH₃

7.94 (d, 1H, J=1.5Hz, 5-positional H on thiazole ring),
9.15 (d, 1H, J=1.5Hz, 2-positional H on thiazole ring),
9.69 (d, 1H, J=8Hz, —CONH)

EXAMPLE 8

1-Acetyloxyethyl
7-[(Z)-2-methoxyimino-2-(thiazxol-4-yl)acetamido]-3-(3-methyl-1,2,4-thiadiazol-5yl)thiomethyl-3-cephem-4-carboxylate Sodium iodide (6.0 g) in acetonitrile (33 ml) was heated to 40° C. After addition of 1-chloroethyl acetate (1.23 g), the mixture was stirred for 30 min at that temperature. The reaction mixture was then treated in the similar manner as in Example 7, giving the title compound (180 mg).

¹H NMR (DMSO-d₆)δ(ppm):

1.50 (d, 3H, J=5.6Hz, —CH—), 2.01, 2.07 (s×2, 3H, —C—CH₃),
                       |                              ||
                       CH₃                            O 2.53 (s, 3H, 3-positional CH₃ on thiadiazole ring),
3.61, 3.81 (ABq, 2H, J=18Hz, C₂—H₂), 3.91 (s, 3H, OCH₃),
4.26 (d, 1H, J=13Hz, C₃—CH),
4.49 (apparent t, 1H, J=14Hz, C₃CH),
5.21 (apparent t, 1H, J=5Hz, C₆—H), 5.90 (m, 1H, C₇—H, 6.95, 7.01 (q×2, 1H, —CH—),
                                         |
                                         CH₃

7.94 (d, 1H, 5-positional H on thiazole ring),
9.15 (d, 1H, 2-positional H on thiazole ring),
9.68 (dd, 1H, —CONH—)

EXAMPLE 9

1-Ethoxycarbonyloxyethyl
7-[(Z)-2-methoxyimino-2-(thiazol-4-yl)acetamido]-3-(3-methyl-1,2,4-thiadiazol-5-yl)thiomethyl-3-cephem-4-carboxylate The title compound was prepared by following the procedure of Example 7 or 8 but using 1-bromoethylethyl carbonate. The contamination of this product with the Δ² isomer was not observed.

The following compounds were prepared from the compound of Example 2 in the same manner as in Examples 3, 7, 8, and 9, respectively.

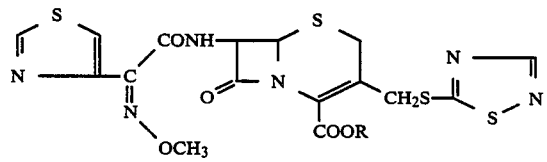

| Example No. | R | ¹H NMR; δ ppm (DMSO—d₆) |
|---|---|---|
| 10 | —CH₂OCOC(CH₃)₃ | 1.15 (s, 9H, (CH₃)₃), 3.62, 3.82 (ABq, 2H, J=18Hz, C₂—H₂), 3.90 (s, 3H, OCH₃), 4.24, 4.63 (ABq, 2H, J=13Hz, C₃—CH₂), 5.20 (d, 1H, J=5Hz, C₆—H), 5.8–6.0 (m, 3H, C₇—H, —COOCH₂O—), 7.94 (d, 1H, J=2Hz, 5-positional H on thiazole ring), 8.72 (s, 1H, 3-positional H on thiadiazole ring), 9.15 (d, 1H, J=2Hz, 2-positional H on thiazole ring), 9.69 (d, 1H, J=8Hz, —CONH—) |
| 11 | —CHOCOC(CH₃)₃<br>\|<br>CH₃ | 1.11, 1.13 (sx2, 9H, —CH₃)₃), 1.50 (m, 3H, —CH—), 3.60 (dd, 1H, J=18, 4Hz, C₂—H), 3.80<br>\|<br>CH₃<br><br>(d, 1H, J=18Hz, C₂—H), 3.90 (s, 3H, OCH₃), 4.27 (dd, 1H, C₃—CH), 4.56 (dd, 1H, C₃—CH), 5.21 (m, 1H, C₆—H), 5.89 (m, 1H, C₇—H), 6.90, 6.99 (qx2, 1H, —CH—),<br>\|<br>CH₃<br>7.94 (d, 1H, J=2Hz, 5-positional H on thiazole ring), 8.72 (s, 1H, 3-positional H on thiadiazole ring), 9.15 (d, 1H, J=2Hz, 2-positional H on thiazole ring), 9.68 (dd, 1H, CONH) |
| 12 | —CHOCOCH₃<br>\|<br>CH₃ | 1.50 (m, 3H, —CH—), 2.01, 2.07 (sx2, 3H, —COCH₃),<br>\|<br>CH₃ |

-continued

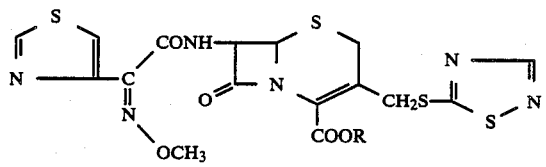

| Example No. | R | $^1$H NMR; δ ppm (DMSO—$d_6$) |
|---|---|---|
|  |  | 3.62, 3.81 (ABq, 2H, J=18Hz, $C_2$—$H_2$), 3.90 (s, 3H, $OCH_3$), 4.26 (d, 1H, J=14Hz, $C_3$—CH), 4.57 (apparent t, 1H, J=14Hz, $C_3$—CH), 5.20 (apparent t, 1H, J=5Hz, $C_6$—H), 5.90 (m, 1H, $C_7$—H), 6.94, 7.02 (qx2, 1H, —C$\underline{H}$— with CH₃), 7.93 (d, 1H, 5-positional H on thiazole ring), 8.72 (sx2, 1H, 3-positional H on thiadiazole ring), 9.15 (d, 1H, 2-positional H on thiazole ring), 9.69 (dx2, 1H, CONH) |
| 13 | —C$\underline{H}$OCOO$C_2H_5$ with $CH_3$ | 1.18, 1.21 (tx2, 3H, —$CH_2C\underline{H}_3$), 1.52 (m, 3H, —C$\underline{H}$— with CH₃), 3.63, 3.82 (ABq, 2H, J=18Hz, $C_2$—$H_2$), 3.90 (s, 3H, $OCH_3$), 4.02–4.35 (m, 3H, —$C\underline{H}_2CH_3$, $C_3$—CH), 4.56, 4.63 (dx2, 1H, J=14Hz, $C_3$—CH), 5.20 (apparent t, 1H, $C_6$—H), 5.90 (m, 1H, $C_7$—H), 6.85, 6.92 (qx2, 1H, —C$\underline{H}$— with CH₃), 7.93 (d, 1H, J=2Hz, 5-positional H on thiazole ring), 8.70, 8.72 (sx2, 1H, 3-positional H on thiadiazole ring), 9.15 (d, 1H, J=2Hz, 2-positional H on thiazole ring), 9.68 (dx2, 1H, CONH) |

EXAMPLE 14

(5-Methyl-2-oxo-1,3-dioxolen-4-yl)methyl 7-[(Z)-2-methoxyimino-2-(thiazol-4-yl)acetamido]-3-(3-methyl-1,2,4-thiadiazol-5-yl)thiomethyl-3-cephem-4-carboxylate 4-Bromomethyl-5-methyl-1,3-dioxolene-2-one (386 mg) was added to a solution of sodium 7-[(Z)-2-methoxyimino-2-(thiazol-4-yl)acetamido]-3-(3-methyl-1,2,4-thiadiazol-5-yl)thiomethyl-3-cephem-4-carboxylate (536 mg) in dimethylformamide (5 ml) at −5° C. The mixture was stirred at this temperature for 1.3 hr and then poured into a mixture of ethyl acetate (130 ml) and water (30 ml, adjusted to pH 3 with dil HCl) with stirring. The ethyl acetate layer was separated, washed successively with water (30 ml, adjusted to pH 3 with dil. HCl), 10% aqueous $K_2HPO_4$ solution (30 ml) twice, and saturated saline water, dried over $MgSO_4$, concentrated in vacuo, and the residue was added dropwise to a mixture of diethyl ether (40 ml) and petroleum ether (40 ml). The formed crystals were filtered, washed with petroleum ether, and dried in vacuo to give the title compound (390 mg).

$^1$H NMR (DMSO-$d_6$)δ(ppm);

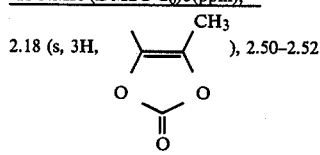

2.18 (s, 3H, ...), 2.50–2.52

(3-positional $CH_3$ on thiadiazole ring, overlapping with peaks due to DMSO used for measurement) 3.59, 3.79 (ABq, 2H, J=18Hz, $C_2$—$H_2$), 3.90 (s, 3H, —$OCH_3$), -continued
4.22, 4.57 (ABq, 2H, J=13.5Hz, $C_3$—$CH_2$),

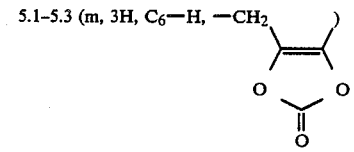

5.1–5.3 (m, 3H, $C_6$—H, —$CH_2$ ...)

5.87 (dd, 1H, $C_7$—H), 7.93
(d, 1H, J=2Hz, 5-positional H on thiazole ring),
9.15 (d, 1H, J=2Hz, 2-positional H on thiazole ring),
9.67 (d, 1H, J=8Hz, —CONH—)

EXAMPLE 15

(5-Methyl-2-oxo-1,3-dioxolen-4-yl)methyl-7-[(Z)-2-methoxyimino-2-(thiazol-4-yl)acetamido]-3-(1,2,4-thiadiazol-5-yl)thiomethyl-3-cephem-4-carboxylate 4-Bromomethyl-5-methyl-1,3-dioxolene-2-one (386 mg) was added to a solution of sodium 7-[(Z)-2-methoxyimino-2-(thiazol-4-yl)acetamido]-3-(1,2,4-thiadiazol-5-yl)thiomethyl-3-cephem-4-carboxylate (522 mg) in N,N-dimethylformamide (5 ml) at −5° C. and the mixture was stirred at this temperature for 1.3 hr. The reaction mixture was then treated in the same manner as in Example 14, giving the title compound (190 mg).

$^1$H NMR (DMSO-$d_6$)δ(ppm);

-continued 2.18 (s, 3H, 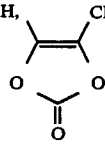CH$_3$),3.61, 3.80 (ABq, 2H, J=18Hz, C$_2$—H$_2$)

3.90 (s, 3H, OCH$_3$), 4.24, 4.64 (ABq, 2H, J=14Hz, C$_3$—CH$_2$), 5.10–5.33

(m, 3H, C$_6$—H, —CH$_2$ 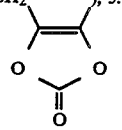), 5.86 (dd, 1H, C$_7$—H), 7.93 (d, 1H, J=2Hz, 5-positional H on thiazole ring),
8.69 (s, 1H, 3-positional H on thiadiazole ring),
9.15 (d, 1H, J=2Hz, 2-positional H on thiazole ring)
9.67 (d, 1H, J=8Hz, —CONH—)

EXAMPLE 16

7-[2-(thiazol-4-yl)glyoxylamino]-3-(1,2,4-thiadiazol-5-yl)thiomethyl-3-cephem-4-carboxylic acid Phosphoryl chloride (1.60 g, 10.5 mmole) was added to a solution of (1, 3-thiazol-4-yl)glyoxylic acid (1.57 g, 10 mmole) in DMA (8 ml) at −10° C. and the mixture was stirred at 0° C. for 1 hr. This mixture was added to a suspension of 7-Amino-3-(1,2,4-thiadiazol-4-yl)thiomethyl-3-cephem-4-carboxylic acid (3.31 g, 10 mmole) and triethylamine (3.03 g, 30 mmole) in CH$_2$Cl$_2$ (30 ml), and the mixture was stirred at 0° C. for 4 hr. To the reaction mixture was added water (30 ml) and acidified with 6N-HCl to pH 2.0. An insoluble material was removed by filtration. The organic layer was separated and the aqueous layer was extracted with CH$_2$Cl$_2$ (100 ml×2). The combined CH$_2$Cl$_2$ layer was dried (MgSO$_4$) and concentrated in vacuo. The residue was triturated with ether (200 ml) to give the title compound (1.34 g).

$^1$H NMR (DMSO-d$_6$)δ ppm: 3.63, 3.79 (ABq, 2H, J=16 Hz), 4.34, 4.63 (ABQ, 2H, J=14 Hz), 5.20 (d, 1H, J=5 Hz), 5.83 (dd, 1H, J=5 Hz, 8 Hz), 8.71 (s, 1H), 8.86 (d, 1H, J=2 Hz), 9.24 (d, 1H, J=2 Hz), 9.89 (d, 1H, J=2 Hz).

EXAMPLE 17

(5-Methyl-2-oxo-1,3-dioxolen-4-yl)methyl 7-[2-(thiazol-4-yl)glyoxylamino]-3-(1,2,4-thiadiazol-4-yl)thiomethyl-3-cephem-4-carboxylate A suspension of 7-[2-(thiazol-4-yl)glyoxylamino]-3-(1,2,4-thiadiazol-5-yl)thiomethyl-3-cephem-4-carboxylic acid (242 mg, 0.5 mmole), KHCO$_3$ (55 mg, 0.55 mmole) and propylene oxide (0.5 ml) in DMF (2.5 ml) was cooled to 5° C. and treated with 4-bromomethyl-5-methyl-1,3-dioxolene-2-one (290 mg, 1.5 mmole). After stirring at 5° C. for 4 hr, the reaction mixture was poured into a mixture of aq HCl (pH 3) (10 ml) and EtOAc (30 ml). The EtOAc layer was separated and washed successively with aq HCl (pH 3) (10 ml), 10% K$_2$HPO$_4$ buffer (pH 7) (10 ml×2) and saturated aq NaCl (10 ml). The EtOAc solution was dried (MgSO$_4$) and concentrated in vacuo. The residue was triturated with ether (50 ml) and the resulting precipitate was filtered to give the title compound (210 mg).

$^1$H NMR (DMSO-d$_6$)δ ppm; 2.19 (s, 3H), 3.65, 3.82 (ABq, 2H, J=18 Hz), 4.26, 4.66 (ABq, 2H, J=13.5 Hz), 5.10–5.34 (m, 3H), 5.86 (dd, 1H, J=5 Hz, 8 Hz), 8.69 (s, 1H), 8.87 (d, 1H, J=2 Hz), 9.25 (d, 1H, J=2 Hz), 9.91 (d, 1H, J=8 Hz).

EXAMPLE 18

(5-Methyl-2-oxo-1,3-dioxolen-4-yl)methyl 7-[(Z)-2-methoxyimino-2-(thiazol-4-yl)acetamido]-3-(1,2,4-thiadiazol-4-yl)thiomethyl-3-cephem-4-carboxylate A solution of CH$_3$ONH$_2$.HCl (27 mg, 0.3 mmole) and (5-Methyl-2-oxo-1,3-dioxolen-4-yl)methyl 7-[2-(thiazol-4-yl)glyoxylamino]-3-(1,2,4-thiadiazol-4-yl)-thiomethyl-3-cephem-4-carboxylate (115 mg, 0.2 mmole) in DMA (1 ml) was stirred at 40° C. for 3.5 hr. The reaction mixture was poured into a mixture of aq HCl (pH 3) (10 ml) and EtOAc (20 ml). The EtOAc layer was separated and washed successively with aq HCl (pH 3) (10 ml), 10% K$_2$HPO$_4$ buffer (pH 7) (10 ml×2) and saturated aq NaCl (10 ml). The EtOAc solution was dried (MgSO$_4$) and concentrated in vacuo. The residue was triturated with ether (50 ml) and the resulting precipitate was filtered to give the title compound (60 mg).

EXAMPLE 19

7-Formamido-3-(1,2,4-thiadiazol-4-yl)-thiomethyl-3-cephem-4-carboxylic acid

A stirred solution of HCOOH (0.92 g, 20 mmole) and Ac$_2$O (2.04 g, 20 mmole) was heated to 50° C. for 1 hr and cooled to room temperature. To the solution was added 7-amino-3-(1,2,4-thiadiazol-4-yl)thiomethyl-3-cephem-4-carboxylic acid (1.65 g, 5 mmole) and stirred at room temperature for 2.5 hr. The reaction mixture was diluted with water (20 ml) and the resulting precipitate was filtered to give the title compound (1.37 g).

$^1$H NMR (DMSO-d$_6$)δ ppm; 3.60, 3.78 (ABq, 2H, J=18 Hz), 4.32 4.61 (ABq, J=13 Hz), 5.12 (d, 1H, J=5 Hz), 5.77 (dd, 1H, J=5 Hz, 8 Hz), 8.13 (s, 1H), 8.71 (s, 1H), 9.05 (d, 1H, J=8 Hz).

EXAMPLE 20

(5-Methyl-2-oxo-1,3-dioxolen-4-yl)methyl 7-formamido-3-(1,2,4-thiadiazol-4-yl)thiomethyl-3-cephem-4-carboxylate A suspension of 7-formamido-3-(1,2,4-thiadiazol-4-yl)thiomethyl-3-cephem-4-carboxylic acid (1.07 g, 3 mmole), KHCO$_3$ (1.0 g, 10 mmole) and propylene oxide (1 ml) in DMF (5 ml) was cooled to 5° C. and treated with 4-bromo-methyl-5-methyl-1,3-dioxolene-2-one (0.87 g, 4.5 mmole). After stirring at 5° C. for 5 hr, the reaction mixture was poured into a mixture of aq HCl (pH 3) (70 ml) and EtOAc (250 ml). The EtOAc layer was separated and washed successively with aq HCl (pH 3) (70 ml×2), 10% K$_2$HPO$_4$ buffer (pH 7) (70 ml×2) and saturated aq NaCl (50 ml). The EtOAc solution was dried (MgSO$_4$) and concentrated in vacuo. The residue was triturated with ether (300 ml) and the resulting precipitate was filtered to give the title compound (0.45 g).

$^1$H NMR (DMSO-d$_6$)δ ppm; 2.17 (s, 3H), 3.62, 3.80 (ABq, 2H, J=18 Hz), 4.24 4.64 (ABq, 2H, J=14 Hz), 5.10–5.38 (m, 3H), 5.77 (dd, 1H, J=5 Hz, 8 Hz), 8.10 (s, 1H), 8.67 (s, 1H), 9.03 (d, 1H, J=8 Hz).

EXAMPLE 21

(5-Methyl-2-oxo-1,3-dioxolen-4-yl)-methyl 7-amino-(1,2,4-thiadiazol-4-yl)thiomethyl-3-cephem-4-carboxylate (5-Methyl-2-oxo-1,3-dioxolen-4-yl)methyl 7-formamido-3-(1,2,4-thiadiazol-4-yl)thiomethyl-3-cephem-4-carboxylate (235 mg) was dissolved in a mixture of methanol (2 ml) and tetrahydrofuran (2 ml) at room temperature and the solution was then cooled with ice. To this solution, conc. HCl (1.0 ml) was added and the mixture was stirred for 2 hr while cooling with ice and for additional 3 hr at room temperature. This reaction mixture was concentrated in vacuo and water (2 ml) was added to the residue. After stirring and then standing, the supernatant was separated by decantation and adjusted to pH 4.0 with conc. NH$_4$OH under cooling with ice. The formed crystals were filtered, washed with cold water (4 ml), and dried in vacuo to give the title compound (100 mg).

$^1$H NMR (DMSO-d$_6$)δppm.

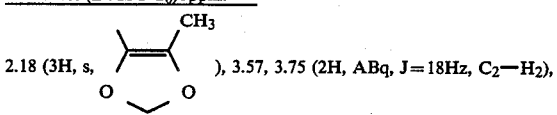

2.18 (3H, s, ), 3.57, 3.75 (2H, ABq, J=18Hz, C$_2$—H$_2$), 4.22, 4.62 (2H, ABq, J=13Hz, C$_3$—CH$_2$),
4.81 (1H, d, J=5Hz, C$_6$—H), 4.99 (1H, d, J=5Hz, C$_7$—H),

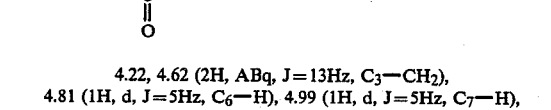

5.15, 5.26 (2H, ABq, J=14Hz, —CH$_2$ ), 8.69 (1H, s, thiadiazole-H)

What is claimed is:

1. The cephem compound represented by the formula

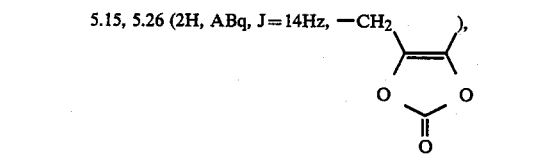

wherein R$^1$ represents hydrogen or methyl, n is 0 or 1 and R represents an alkanoyloxyalkyl, alkoxycarbonyloxyalkyl, or (5-alkyl-2-oxo-1,3-dioxolen-4-yl)methyl group and salts thereof.

2. The cephem compound or the salt thereof according to claim 1, which is a syn isomer.

3. The cephem compound of claim 1, wherein R$^1$ is hydrogen and n is 0.

4. The cephem compound of claim 1, wherein R$^1$ is methyl and n is 0.

5. The cephem compound of claim 3, wherein R is an alkanoyloxyalkyl or alkoxycarbonyloxyalkyl group.

6. The cephem compound of claim 4, wherein R is an alkanoyloxyalkyl or alkoxycarbonyloxyalkyl group.

7. The cephem compound of claim 3, wherein R is a (5-alkyl-2-oxo-1,3-dioxolen-4-yl)methyl group.

8. The cephem compound of claim 4, wherein R is a (5-alkyl-2-oxo-1,3-dioxolen-4-yl)methyl group.

9. Pivaloyloxymethyl 7-[(Z)-2-methoxyimino-2-(thiazol-4-yl)acetamido]-3-(3-methyl-1,2,4-thiadiazol-5-yl)thiomethyl-3-cephem-4-carboxylate.

10. 1-Ethoxycarbonyloxyethyl 7-[(Z)-2-methoxyimino-2-(thiazol-4-yl)acetamido]-3-(3-methyl-1,2,4-thiadiozol-5-yl)thiomethyl-3-cephem-4-carboxylate.

11. 1-Pivaloyloxyethyl 7-[(Z)-2-methoxyimino-2-(thiazol-4-yl)acetamido]-3-(3-methyl-1,2,4-thiadiazol-5-yl)thiomethyl-3-cephem-4-carboxylate.

12. 1-Acetyloxyethyl 7-[(Z)-2-methoxyimino-2-(thiazol-4-yl)acetamido]-3-(3-methyl-1,2,4-thiadiazol-5-yl)thiomethyl-3-cephem-4-carboxylate.

13. (5-Methyl-2-oxo-1,3-dioxolen-4-yl)methyl 7-[(Z)-2-methoxyimino-2-(thiazol-4-yl)acetamido]-3-(3-methyl-1,2,4-thiadiazol-5-yl)thiomethyl-3-cephem-4-carboxylate.

14. Pivaloyloxymethyl 7-[(Z)-2-methoxyimino-2-(thiazol-4-yl)acetamido]-3-(1,2,4-thiadizol-5-yl)thiomethyl-3-cephem-4-carboxylate.

15. 1-Pivaloyloxyethyl 7-[(Z)-2-methoxyimino-2-(thiazol-4-yl)acetamido]-3-(1,2,4-thiadiazol-5-yl)-thiomethyl-3-cephem-4-carboxylate.

16. 1-Acetyloxyethyl 7-[(Z)-2-methoxyimino-2-(thiazol-4-yl)acetamido-3-(1,2,4-thiadiazol-5-yl)-thiomethyl-3-cephem-4-carboxylate.

17. 1-Ethoxycarbonyloxyethyl 7-[(Z)-2-methoxyimino-2-(thiazol-4-yl)acetamido]-3-(1,2,4-thiadiazol-5-yl)-thiomethyl-3-cephem-4-carboxylate.

18. (5-Methyl-2-oxo-1,3-dioxolen-4-yl)methyl 7-[(Z)-2-methoxyimino-2-(thiazol-4-yl)acetamido]-3-(1,2,4-thiadiazol-5-yl)thiomethyl-3-cephem-4-carboxylate.

19. A pharmaceutical composition for preventing or treating infectious diseases which comprises a cephem compound represented by the formula

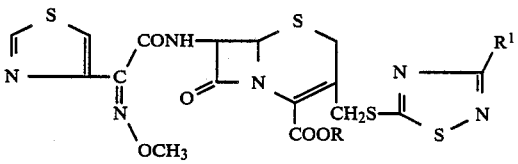

wherein R$^1$ represents hydrogen or methyl and R represents an alkanoxyloxy alkyl, alkoxycarbonyloxyalkyl or 5-alkyl-2-oxo-1,3-dioxalen-4-yl)methyl group or a pharmaceutically acceptable salt thereof, as an active ingredient.

20. A method of preventing or treating bacterial infectious diseases which comprises administering an effective amount of the cephem compound or the pharmaceutically acceptable salt of claim 1 to a patient.

21. A cephem compound represented by the general formula

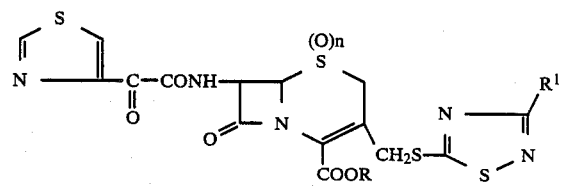

wherein R¹ represents hydrogen or methyl, R represents an alkanoyloxyalkyl ester, alkoxycarbonyloxyalkyl ester or (5-alkyl-2-oxo-1,3-dioxolen-4-yl) methyl ester and n is 0 or 1, or a salt thereof.

22. (5-Methyl-2-oxo-1,3-dioxolen-4-yl)methyl 7-[2-(thiazol-4-yl)glyoxylamino]-3-(1,2,4-thiadiazol-4-yl)thiomethyl-3-cephem-4-carboxylate.

23. 7-[2-(Thiazol-4-yl)glyoxylamino]-3-(1,2,4-thiadiazol-4-yl)thiomethyl-3-cephem-4-carboxylic acid.

UNITED STATES PATENT AND TRADEMARK OFFICE
CERTIFICATE OF CORRECTION

PATENT NO. : 4,761,409
DATED : August 2, 1988
INVENTOR(S) : Hirotada YAMADA et al It is certified that error appears in the above-identified patent and that said Letters Patent is hereby corrected as shown below:

In the ABSTRACT and CLAIM 1, correct the structural formula to read as follows:

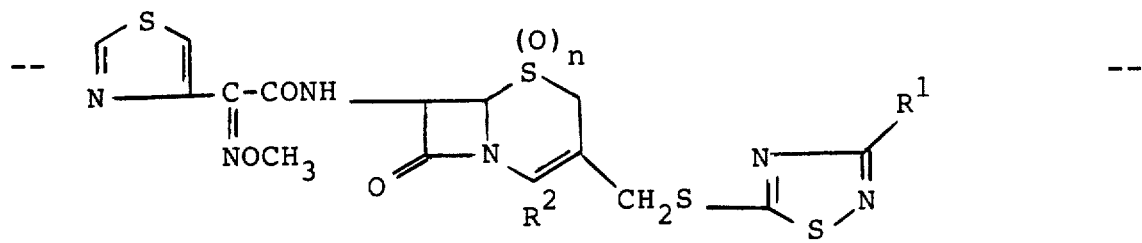

Signed and Sealed this

Second Day of April, 1991

Attest:

HARRY F. MANBECK, JR.

Attesting Officer

Commissioner of Patents and Trademarks